(12) United States Patent
Smith et al.

(10) Patent No.: US 10,001,447 B2
(45) Date of Patent: Jun. 19, 2018

(54) USING 3D COMPUTED TOMOGRAPHY TO ANALYZE SHAPED CHARGE EXPLOSIVES

(71) Applicant: Halliburton Energy Services, Inc., Houston, TX (US)

(72) Inventors: John Norris Smith, Burleson, TX (US); Patrick William Powell, Nemo, TX (US); Corbin Sean Glenn, Burleson, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 0 days. days.

(21) Appl. No.: 14/901,772

(22) PCT Filed: May 13, 2015

(86) PCT No.: PCT/US2015/030523
§ 371 (c)(1),
(2) Date: Dec. 29, 2015

(87) PCT Pub. No.: WO2016/118182
PCT Pub. Date: Jul. 28, 2016

(65) Prior Publication Data
US 2016/0370305 A1 Dec. 22, 2016

Related U.S. Application Data

(60) Provisional application No. 62/107,105, filed on Jan. 23, 2015.

(51) Int. Cl.
*G01N 23/00* (2006.01)
*G01N 23/04* (2018.01)
(Continued)

(52) U.S. Cl.
CPC ......... *G01N 23/046* (2013.01); *G01N 33/222* (2013.01); *G01V 5/08* (2013.01);
(Continued)

(58) Field of Classification Search
CPC ....... G01N 2223/302; G01N 2223/419; G01N 2223/633; G01N 23/046; G01N 33/222
See application file for complete search history.

(56) References Cited

U.S. PATENT DOCUMENTS

2006/0185430 A1 8/2006 Yogeswaren
2006/0241412 A1* 10/2006 Rinck .................... A61B 6/481
600/431
(Continued)

OTHER PUBLICATIONS

International Search Report and Written Opinion for PCT/US2015/030523 dated Oct. 20, 2015.

*Primary Examiner* — Dani Fox
(74) *Attorney, Agent, or Firm* — McDermott Will & Emery LLP (57) ABSTRACT

A method may include positioning at least one calibration disk in a computed tomography (CT) scanner and positioning a pellet in the CT scanner. The at least one calibration disk and the pellet may both be made of a same powder exhibiting a known density. The method may further include scanning the at least one calibration disk and the pellet using the CT scanner to obtain one or more CT images of the pellet and the at least one calibration disk, and comparing a density of the pellet with the known density of the at least one calibration disk based on the one or more CT images.

20 Claims, 9 Drawing Sheets

(51) Int. Cl.
  *G01V 5/08*      (2006.01)
  *G01V 13/00*     (2006.01)
  *G01N 33/22*     (2006.01)

(52) U.S. Cl.
  CPC ....... *G01V 13/00* (2013.01); *G01N 2223/302* (2013.01); *G01N 2223/303* (2013.01); *G01N 2223/419* (2013.01); *G01N 2223/616* (2013.01); *G01N 2223/633* (2013.01)

(56) References Cited

U.S. PATENT DOCUMENTS

| | | |
|---|---|---|
| 2009/0116336 A1 | 5/2009 | Summerfield et al. |
| 2013/0028371 A1* | 1/2013 | Derzhi ................ G01N 23/087 378/5 |
| 2013/0073207 A1 | 3/2013 | Ganz |
| 2013/0301794 A1 | 11/2013 | Grader et al. |

* cited by examiner

USING 3D COMPUTED TOMOGRAPHY TO ANALYZE SHAPED CHARGE EXPLOSIVES

CROSS-REFERENCE TO RELATED APPLICATIONS

This application claims priority under 35 U.S.C. § 119 to Provisional Application No. 62/107,105 filed on Jan. 23, 2015, in the United State Patent and Trademark Office (USPTO), which is incorporated herein by reference in its entirety.

BACKGROUND

After drilling the various sections of a subterranean wellbore that traverses a formation, individual lengths of relatively large diameter metal tubulars are typically secured together to form a casing string that is positioned within the wellbore. This casing string increases the integrity of the wellbore and provides a path for producing fluids from the producing intervals to the surface. Conventionally, the casing string is cemented within the wellbore. To produce fluids into the casing string, hydraulic openings or perforations must be made through the casing string, the cement, and a short distance into the formation.

Typically, these perforations are created by detonating a series of shaped charges that are disposed within the casing string and are positioned adjacent to the formation. Specifically, one or more perforating guns are loaded with shaped charges that are connected with a detonator via a detonating cord. The perforating guns are then connected within a tool string that is lowered into the cased wellbore at the end of a tubing string, wireline, slickline, coiled tubing or other conveyance. Once the perforating guns are properly positioned in the wellbore such that the shaped charges are adjacent to the formation to be perforated, the shaped charges may be detonated, thereby creating the desired hydraulic openings.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is related to downhole tools used in the oil and gas industry and, more particularly, to improving the development process and fabrication of shaped charges by conducting non-destructive analyses on pressed explosive powder.

According to the embodiments disclosed herein, a pellet of explosive powder used in a shaped charge may be fabricated and analyzed to determine density variations. Based on the analysis, the fabrication techniques of subsequent pellets may be modified to increase the density and/or make the density more uniform throughout the pellet. As will be appreciated, this may result in a better performing shaped charge. It should be noted that, although embodiments herein are directed to non-destructively analyzing explosive powders, the present disclosure is not limited only to explosive powders. Rather, other types of powdered substances including, but not limited to, ceramic powders, pharmaceutical powders, powdered metals, powdered foods, or the like may also be analyzed, without departing from the scope of the disclosure. Further, although embodiments below are directed to analyzing density variations, it should be noted that the embodiments below may also be used to analyze physical properties or characteristics, such as, mass, volume, viscosity, porosity, mass, color, luster, voids, fissures, and the like, without departing from the scope of the disclosure. Additionally, embodiments below may not be limited to analyzing shaped charges, and may be used to analyze physical properties or characteristics of any object, such as fluids, plastics, circuit boards, or semiconductor materials, food, clothing, or the like.

Figure 1:
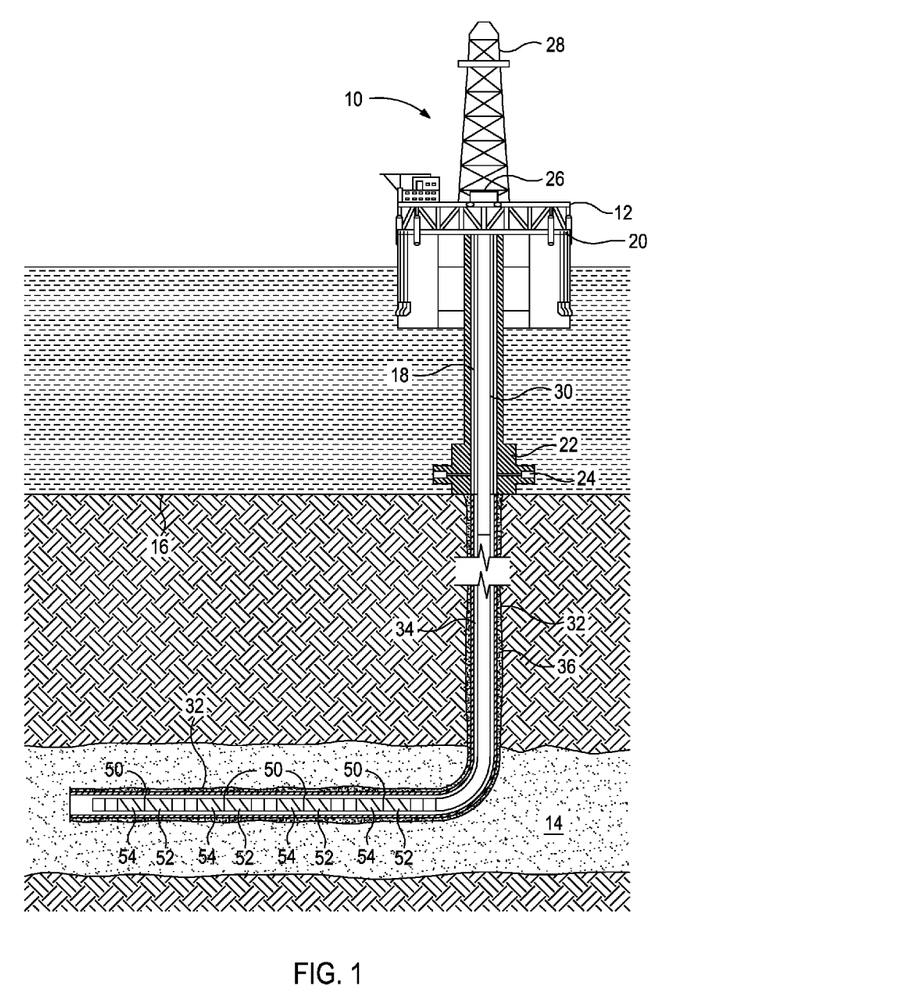
FIG. 1 is a well system that may employ shaped charges optimized through the principles of the present disclosure.

Referring to FIG. 1, a well system 10 is illustrated that may employ shaped charges that are optimized through the principles of the present disclosure, according to one or more embodiments. As illustrated, a semi-submersible platform 12 may be centered over a submerged oil and gas formation 14 located below a sea floor 16. A subsea conduit 18 may extend from a deck 20 of the platform 12 to a wellhead installation 22, which may include one or more subsea blowout preventers 24. The platform 12 may have a rotary table 26 and a derrick 28 for raising and lowering pipe strings, such as a work string 30.

A wellbore 32 may extend through the various earth strata, including the formation 14. A casing 34 may be cemented within the wellbore 32 with cement 36. The work string 30 may include various tools, such as a plurality of perforating gun assemblies 50. When it is desired to perforate the formation 14, the work string 30 may be lowered through the casing 34 until the perforating guns 50 are positioned relative to the formation 14. Thereafter, shaped charges 52, 54 within the perforating guns 50 may be sequentially fired, either in an uphole to downhole direction or a downhole to uphole direction. Upon detonation, liners of the shaped charges 52, 54 form jets that may create a spaced series of perforations extending outwardly through the casing 34, the cement 36 and into the formation 14, thereby allowing fluid communication between the formation 14 and the wellbore 32.

Generally, the shaped charges 52, 54 may comprise compressed or pressed explosive powder. Prior to deployment into the perforating guns 50, the shaped charges 52, 54 may be pressed into desired shapes that may be accommodated and otherwise positioned within the perforating guns 50. Pressing the shaped charges 52, 54, however, can often result in inconsistencies in the density of the shaped charges 52, 54, and an inconsistent density can result in underperformance of the shaped charge 52, 54 in the field.

According to embodiments of the present disclosure, the development process of shaped charges may be improved by non-destructively analyzing the pressed explosive powder using computed tomography. Computed tomography (CT), commonly known in the medical field as CAT scanning ("computerized axial tomography" or "computer assisted tomography"), is a non-destructive technology that provides an image of the internal structure and composition of an object, such as a shaped charge of the present disclosure. What makes the technology unique is the ability to obtain imaging which represents cross-sectional axial or longitudinal slices through the object. This is accomplished through the reconstruction of a matrix of x-ray attenuation coefficients by a dedicated computer system, which controls a CT scanner. Essentially, the CT scanner is a device that detects density differences in a volume of material of varying thicknesses. The resulting images and quantitative data that are produced reflect volume-by-volume (voxel) variations displayed as gray levels of contrasting CT numbers. However, the CT scanner may not provide the density value at one or more locations in the material. The CT scanner will take two dimensional slice images which may then be reconstructed into two-dimensional (2D) or three-dimensional (3D) images. The produced images represent the internal structure and composition of the core of the object being analyzed.

Example embodiments disclosed herein may be directed to a method of examining density variations in a pellet formed from an explosive powder and used as a shaped charge. The performance of a shaped charge may be directly influenced by the density of the pellet. More particularly, the higher the density of the pellet and the more uniform the density is throughout the pellet, the better the performance of the shaped charge will be in the field.

Figure 2:
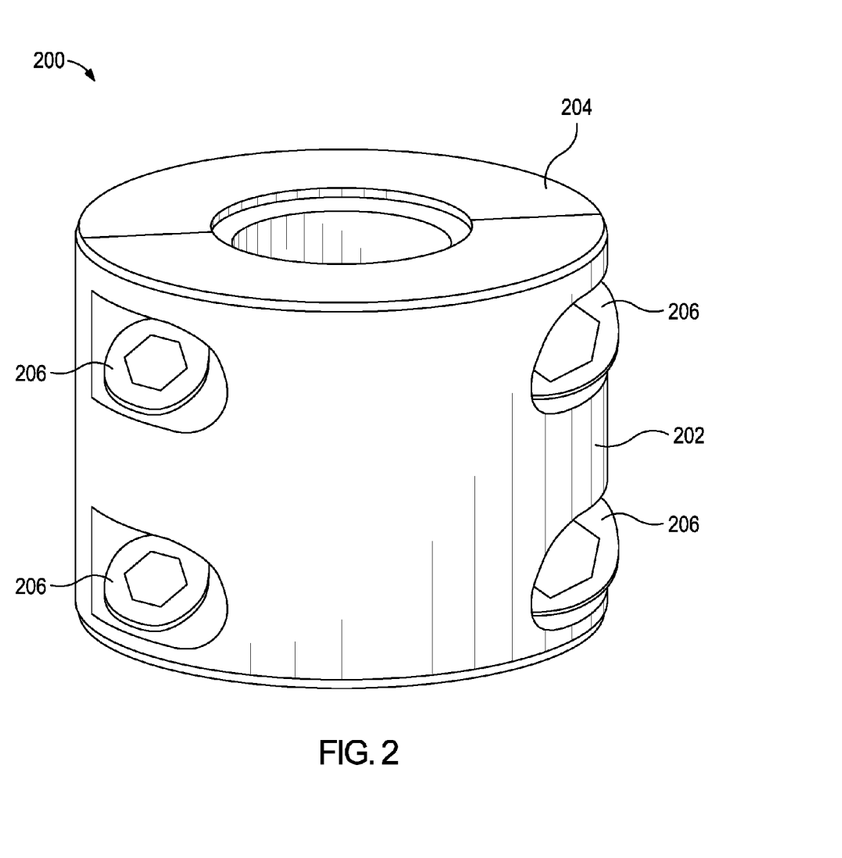
FIG. 2 illustrates an isometric view of a split die body used to press explosive powder into a pellet.

FIG. 2 illustrates an isometric view of a split die body 200 that may be used to press explosive powder into a pellet (not shown) that may be subsequently analyzed for density determination. Again, however, as briefly mentioned above, the explosive powder may be replaced with other types of powders or powdered substances including, but not limited to, ceramic powders, pharmaceutical powders, powdered metals, powdered foods, or the like that may require similar density analysis. The split die body 200 may comprise a molding device or apparatus that operates to press the pellet into a desired shape that matches the shape of the internals of a particular shaped charge (e.g., the shaped charges 52, 54 of FIG. 1). Accordingly, the resulting pellet may be representative of a given type of shaped charge used in a perforating operation, such as that described above.

As illustrated, the split die body 200 may comprise a two-piece structure that replicates the internals of the case of a given shaped charge. For instance, the split die body 200 may comprise pieces 202 and 204 that may be removably joined or affixed to each other using one or more fasteners 206, such as nuts, bolts, screws, clips, or the like. Similar to the pressing of a given shaped charge for downhole use, the pellet may be pressed in the split die body 200 using an explosive punch. Consequently, the process to create the pellet may be the same process used in pressing and creating a shaped charge. One difference, however, is the use of the two-piece die, which allows the pressed pellet to be subsequently removed from the split die body 200 and scanned, whereas a typical shaped charge is permanently pressed into its housing for subsequent downhole use.

Figure 3:
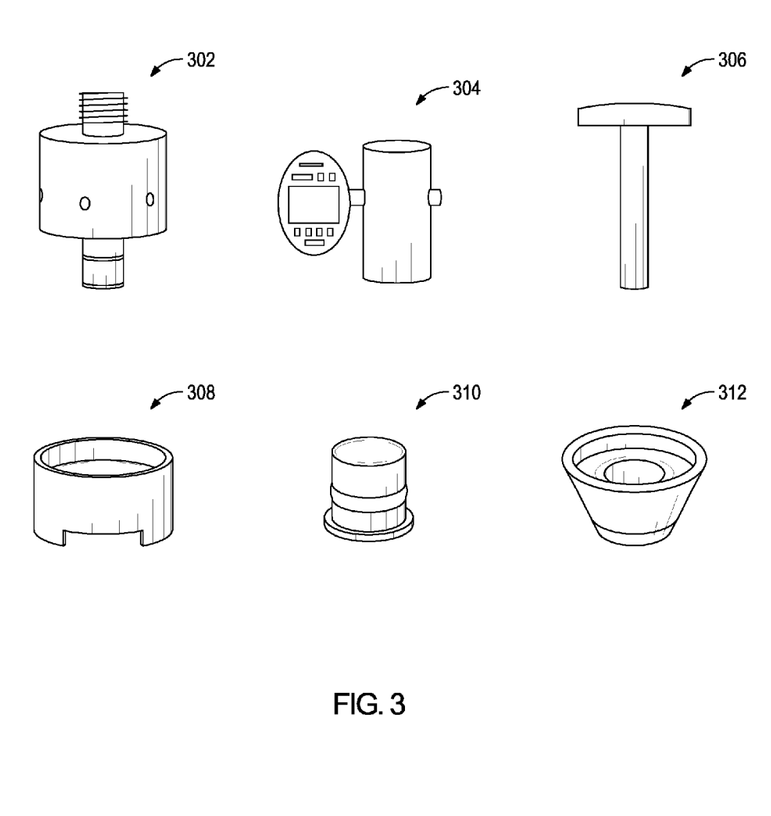
FIG. 3 illustrates component parts for a calibration disk tooling.

FIG. 3 illustrates an isometric view of various component parts for a calibration disk tooling 300. The calibration disk tooling 300 may be used to create calibration disks from the same explosive powder used to make the pellet in the split die body 200 of FIG. 2. The calibration disk tooling 300 may comprise a molding device that includes various component parts including a punch 302, a die body 304, a disk removal punch 306, a die body base 308, a bottom plug 310, and/or a disk removal base 312. Each of these components may be secured together and otherwise interact to form calibration disks that exhibit a known density or density profile. To accomplish this, the calibration disk tooling 300 may be configured to vacuum press a known mass of the explosive powder to a known volume at various known tonnages. As a result, the density of each calibration disk may be calculated and otherwise ascertained and subsequently used as corresponding density reference points in comparison against the pellet made in the split die body 200. Accordingly, the resulting calibration disks may be characterized as a type of calibration tool for the pellets. The density of the calibration disks may be uniform or the same throughout the calibration disks. Stated otherwise, the density of the calibration disks at any location in/on the calibration disks may be the same.

Figure 4:
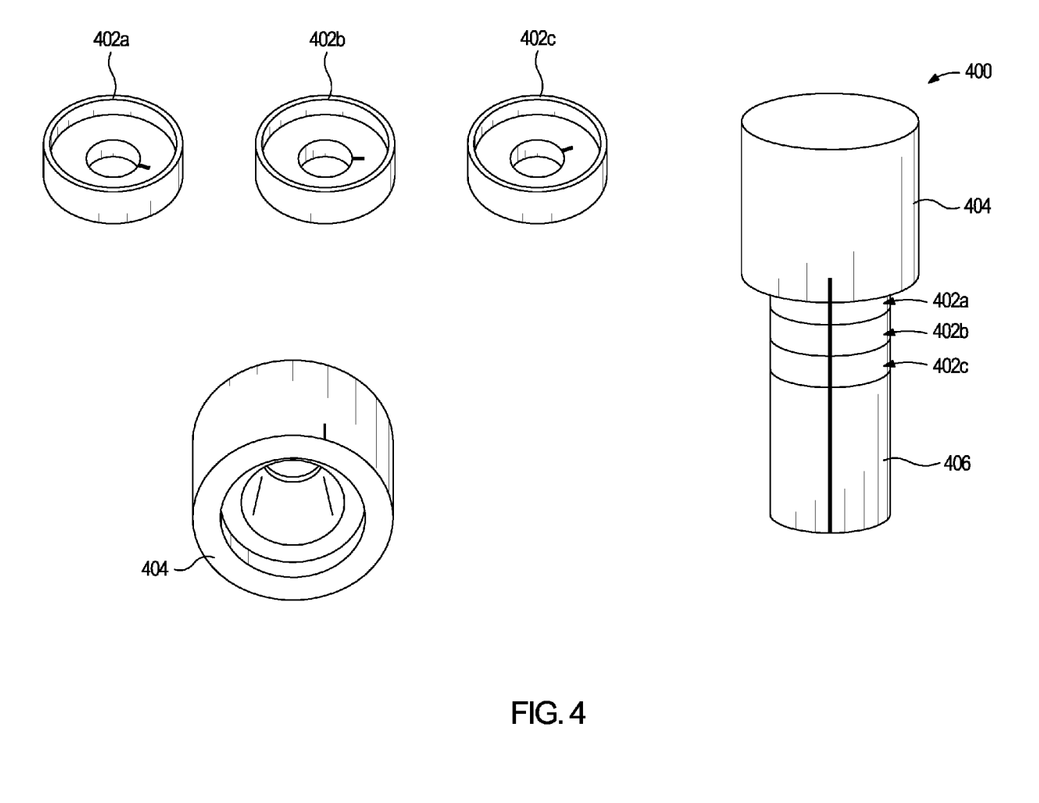
FIG. 4 illustrates isometric views of an exemplary computed tomography (CT) fixture and its different components.

FIG. 4 illustrates isometric views of component parts of an exemplary CT fixture 400 and its different components, according to one or more embodiments. The CT fixture 400 may be configured to house the pellet made by the split die body 200 of FIG. 2 and one or more calibration disks made by the calibration disk tooling 300 of FIG. 3. Once properly positioned within the CT fixture 400, as discussed below, the pellet and the calibration disks may be subjected to scanning in a conventional CT scanner (not shown).

As illustrated, the CT fixture 400 may include a plurality of disk fixtures 402a-c and a pellet fixture 404. Each disk fixture 402a-c may be configured to receive and seat a corresponding calibration disk or the bottom of the pellet, and the pellet fixture 404 may be configured to receive and/or seat the pellet. The disk fixtures 402a-c and the pellet fixture 404 may be made of a material having a density that is lower than the density of the pellet and the calibration disks. As a result, the CT fixture 400 may be imaged relatively less vividly by the CT scanner as compared to the images of the pellet and the calibration disks. Consequently, the image of the CT fixture 400 will have a reduced influence on the images of the pellet and the calibration disks. In at least one embodiment, for example, some or all of the disk fixtures 402a-c and the pellet fixture 404 may be made of machinable foam, but could alternatively be made of other low-density materials. Each disk fixture 402a-c may have the same dimensions (e.g., length, breath, height, diameter, thickness) so that each may provide the same amount of scattering of x-rays during the scanning process.

In some embodiments, as illustrated, the disk fixtures 402a-c and the pellet fixture 404 may be stackable and otherwise arranged longitudinally for ease of scanning in the CT scanner. In the illustrated embodiment, the second and third disk fixtures 402b and 402c may be configured to receive and seat two corresponding calibration disks, and the first disk fixture 402a may be configured to receive the bottom of the pellet. The pellet fixture 404 may then be lowered over the pellet to encapsulate and otherwise cover the top portions of the pellet. While three disk fixtures 402a-c are shown in FIG. 4, it will be appreciated that any number of disk fixtures and corresponding calibration disks may be used in the CT fixture 400, without departing from the scope of the disclosure.

In the illustrated embodiment, the CT fixture 400 may also include a pedestal 406 on which the disk fixtures 402a-c, and the pellet fixture 404 may be sequentially stacked. The pedestal 406 may also be composed of a material similar to the disk fixtures 402a-c and the pellet fixture 404. The pedestal 406 may provide a separation between the lowermost disk fixture (402c in this case) and the floor or base of the CT scanner on which the CT fixture 400 is placed for the scanning operation. The separation may minimize the scattering of the x-rays and improve the quality of the CT image.

Figure 5A:
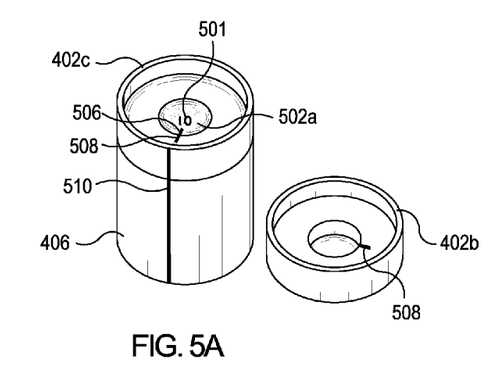
FIGS. 5A, 5B, and 5C illustrate an exemplary loading process for the CT fixture of FIG. 4.
Figure 5B:
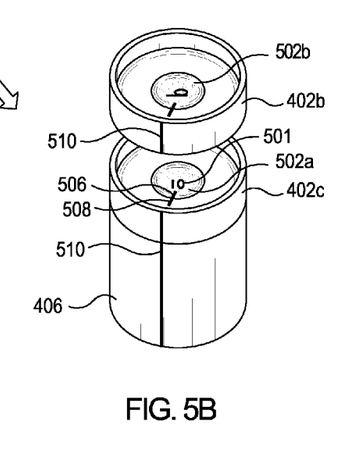
Figure 5C:
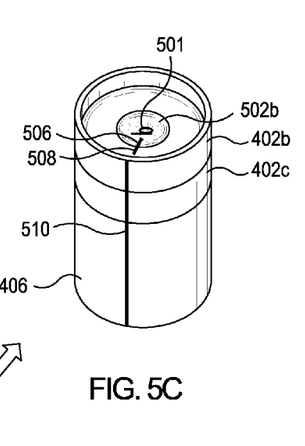

FIGS. 5A, 5B, and 5C illustrate an exemplary loading process for the CT fixture 400, according to one or more embodiments disclosed. More particularly, FIG. 5A shows the loading of a first calibration disk 502a into the third disk fixture 402c and the loading of a second calibration disk 502b into the second disk fixture 402b. In some embodiments, each calibration disk 502a, 502b may have an identifier 501 placed on a top face thereof. The identifier 501 may comprise a marking, such as a number or letter that may identify the specific calibration disk being handled or used, and the top face, the bottom face and/or the lateral faces of the calibration disk.

As illustrated, the first calibration disk 502a is loaded into the third disk fixture 402c and the identifier 501 "10" is exposed for reference. It should be noted that, although embodiments disclosed herein refer to using disk-shaped articles for calibration purposes, the shape of the articles used for calibration purposes are not limited thereto and that the shape and size of the calibration articles may be chosen as per design requirements. For example, the calibration disks 502a,b may alternatively be spherical, cubical, cuboidal, cylindrical, prismatic, conical, pyramidal, or the like. The disk fixtures 402a-c and the pellet fixture 404 may be modified accordingly to receive the corresponding calibration article.

As illustrated in FIGS. 5A, 5B, and 5C, an orientation mark 506 may be placed on each calibration disk 502a,b, for example, at or adjacent an outer circumferential edge thereof. A corresponding orientation mark 508 may be placed on each disk fixture 402b,c. While assembling the calibration disks 502a,b into the disk fixtures 402b,c, respectively, the orientation marks 506 and 508 may be aligned to ensure consistent orientation of the calibration disks 502a,b and the disk fixtures 402b,c from scan to scan.

Similarly, a body orientation mark 510 may be placed on the outer surface of each disk fixture 402b,c and the pedestal 406. For instance, the body orientation mark 510 may be a longitudinally extending line. The body orientation mark 510 may ensure consistent angular orientation between the disk fixtures 402b,c and the pedestal 406 when stacking the disk fixtures 402b,c on the pedestal 406. Although not illustrated, it will be understood that similar orientation marks 506, 508, and 510 may be placed on the first disk fixture 402a and the third calibration disk 502c.

Still referring to FIGS. 5A-C, the loading process may include placing the first calibration disk 502a in the third disk fixture 402c and aligning the respective orientation marks 506, 508. The second disk fixture 402b may then be stacked on the third disk fixture 402c and the body orientation marks 510 on the outer surfaces of the second and third disk fixtures 402b,c may be aligned with each other. The second calibration disk 502b may then be placed within the second disk fixture 402b and aligned therewith using the orientation marks 506, 508. The first disk fixture 402a may then be stacked on the second disk fixture 402b and the body orientation marks 510 on the outer surfaces of the first and second disk fixtures 402a,b may be aligned with each other.

Figure 6A:
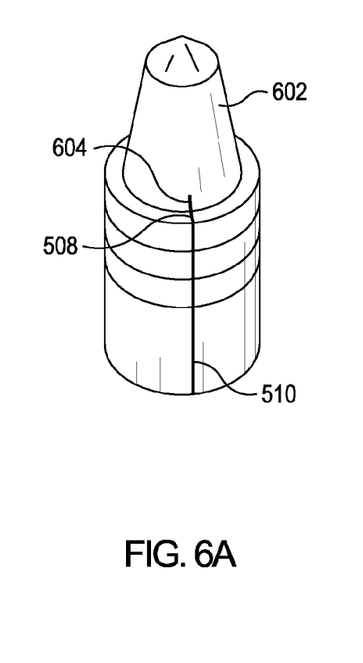
FIGS. 6A, 6B, and 6C illustrate an exemplary process of loading a pellet into the CT fixture of FIG. 4.
Figure 6B:
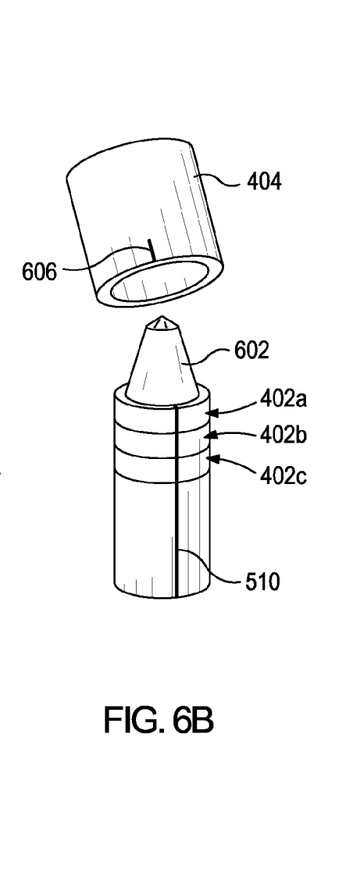
Figure 6C:
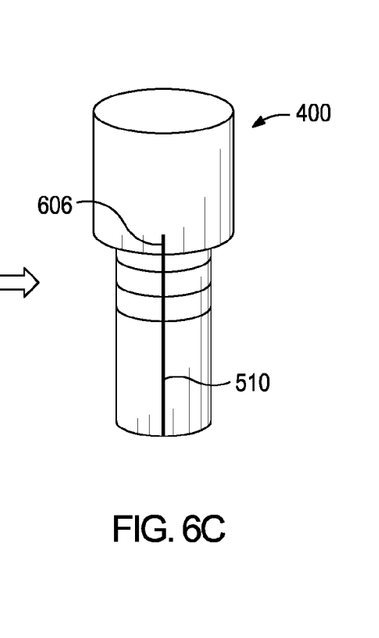

FIGS. 6A, 6B, and 6C illustrate an exemplary process of loading a pellet 602 into the CT fixture 400, according to one or more embodiments disclosed. As illustrated in FIG. 6A, the pellet 602 may be placed on top of the first disk fixture 402a, which may define a cavity or orifice designed to receive and seat the pellet 602. The pellet 602 may also include an orientation mark 604 that may be angularly aligned with the body orientation mark 510 on the outer surface of the CT fixture 400. Additionally or alternatively, the orientation mark 604 may be angularly aligned with the orientation mark 508 on the first disk fixture 402a. As shown in FIG. 6B, the pellet fixture 404 may be lowered over the pellet 602 to encapsulate the pellet 602 within the CT fixture 400. In some embodiments, the pellet fixture 404 may include a body orientation mark 606 positioned on its exterior surface. The pellet fixture 404 may be rotated until the body orientation mark 606 aligns with and otherwise becomes part of the body orientation mark 510 on the body of the CT fixture 400.

In an embodiment, the body orientation mark 510 may be used to accurately align the CT fixture 400 within the CT scanner for scanning operations. FIG. 6C illustrates the CT fixture 400 as properly assembled. Those skilled in the art will readily appreciate that the number of disk fixtures and calibration disks disclosed above are merely one example, and the number may be increased or decreased without departing from the scope of the disclosure.

Figure 7:
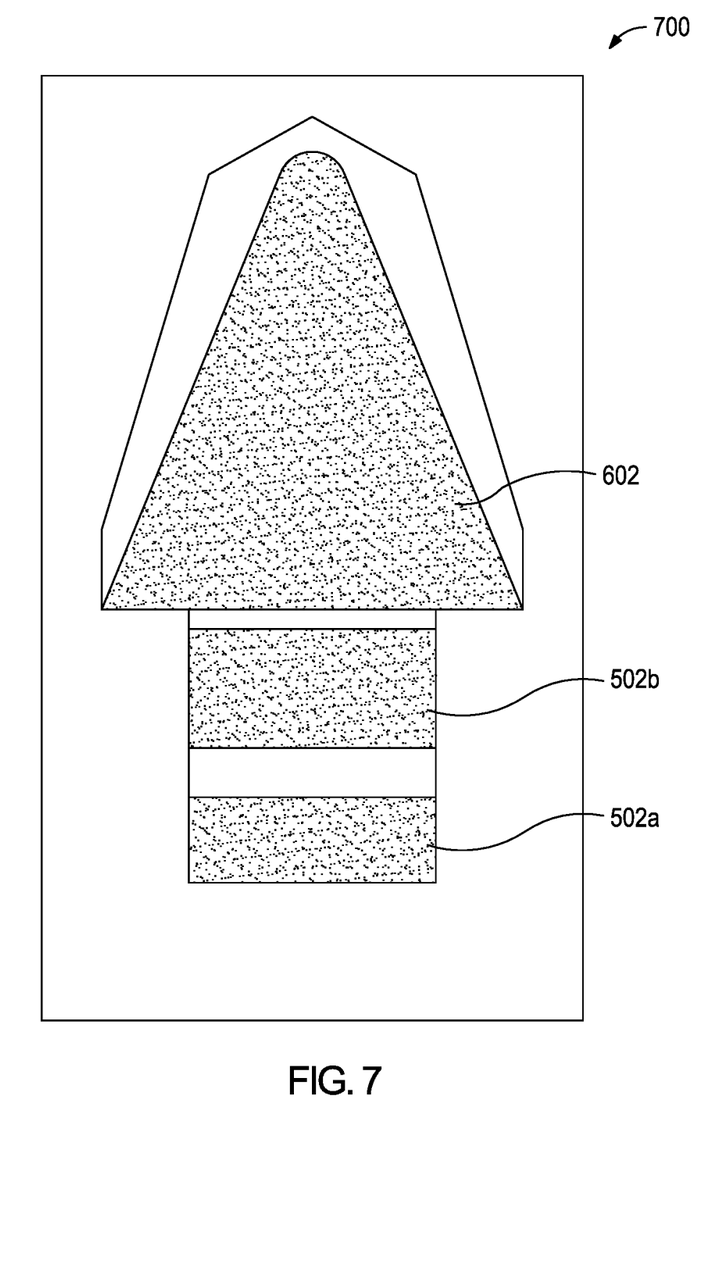
FIG. 7 illustrates a CT image of the pellet of FIG. 6 and the first and second calibration disks of FIG. 5 following a CT scan.

Referring now to FIG. 7, with continued reference to FIGS. 5A-5C and 6A-6C, illustrated is a CT image 700 of the pellet 602 and the first and second calibration disks 502a, 502b following a CT scan, according to one or more embodiments disclosed. In some embodiments, the CT image 700 may be 2D, but in other embodiments, the CT image 700 may be 3D. The CT image 700 may be analyzed to determine density differences (if any) between the pellet 602 and the first and second calibration disks 502a, 502b. More particularly, since the corresponding densities of the first and second calibration disks 502a, 502b are known, a density profile of the pellet 602 may be determined using the densities of the first and second calibration disks 502a, 502b as reference points. As will be appreciated, this may prove advantageous in designing a more dependable shaped charge.

In an embodiment, numerical analysis may be performed on the CT image 700 to distinguish between minor color variations in the image that are not detectable to the human eye. Herein, "numerical analysis" refers to the use of a number range to represent a color scale. For example, if the color scale of the CT scan potentially has up to 65,000 different colors or grey-scales, a corresponding numerical analysis may involve assigning a number value between 0 and 64,999 to pixels of the CT image. For grey-scale images, a low number value (e.g., 0) may correspond to a darkest black pixel while a high number value (e.g., 64,999) may correspond to a brightest white pixel. Based on the differences in the color in the CT image of the calibration disk and the pellet, density differences between the calibration disks and the pellet may be determined. This may in turn determine the density at various locations in the pellet.

Figure 8:
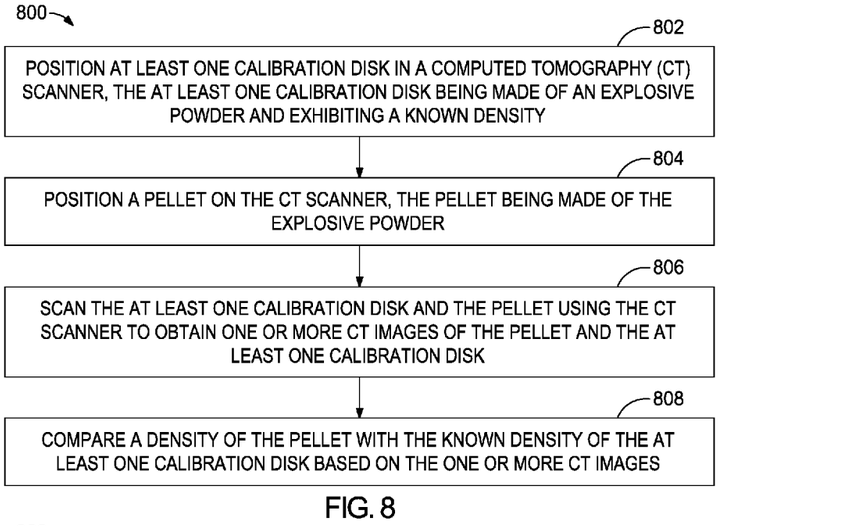
FIG. 8 is a flowchart of an exemplary method for analyzing a pellet.

FIG. 8 is a flowchart of a method 800 for analyzing a pellet. The method may include positioning at least one calibration disk made of an explosive powder and exhibiting a known density in a computed tomography (CT) scanner, as at 802, positioning a pellet made of the explosive powder in the CT scanner, as at 804, scanning the at least one calibration disk and the pellet using the CT scanner to obtain one or more CT images of the pellet and the at least one calibration disk, as at 806, and comparing a density of the pellet with the known density of the at least one calibration disk based on the one or more CT images, as at 808.

Figure 9:
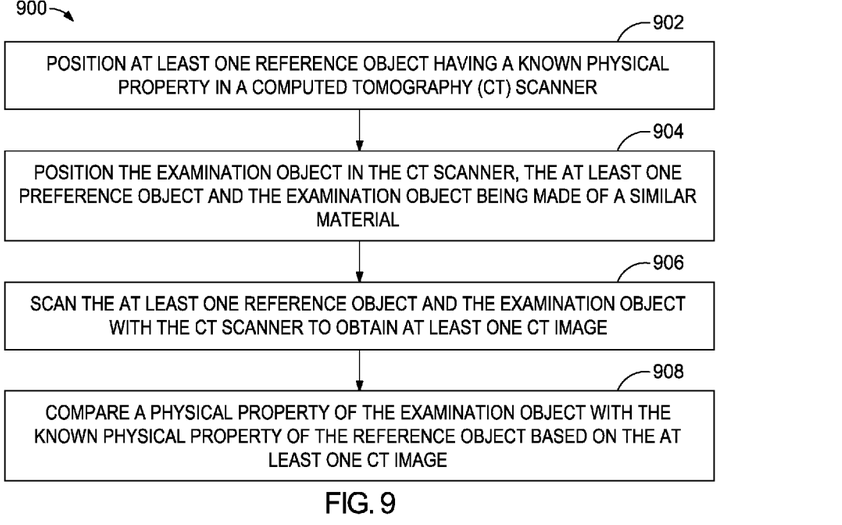
FIG. 9 is a flowchart of an exemplary method for examining an object.

FIG. 9 is a flowchart of a method 900 for examining an object. The method may include positioning at least one reference object having a known physical property in a computed tomography (CT) scanner, as at 902, positioning the examination object made of a material similar to a material of the at least one reference object in the CT scanner, as at 904, scanning the at least one reference object and the examination object with the CT scanner to obtain at least one CT image, as at 906, and, comparing a physical property of the examination object with the known physical property of the reference object based on the at least one CT image, as at 908.

Figure 10:
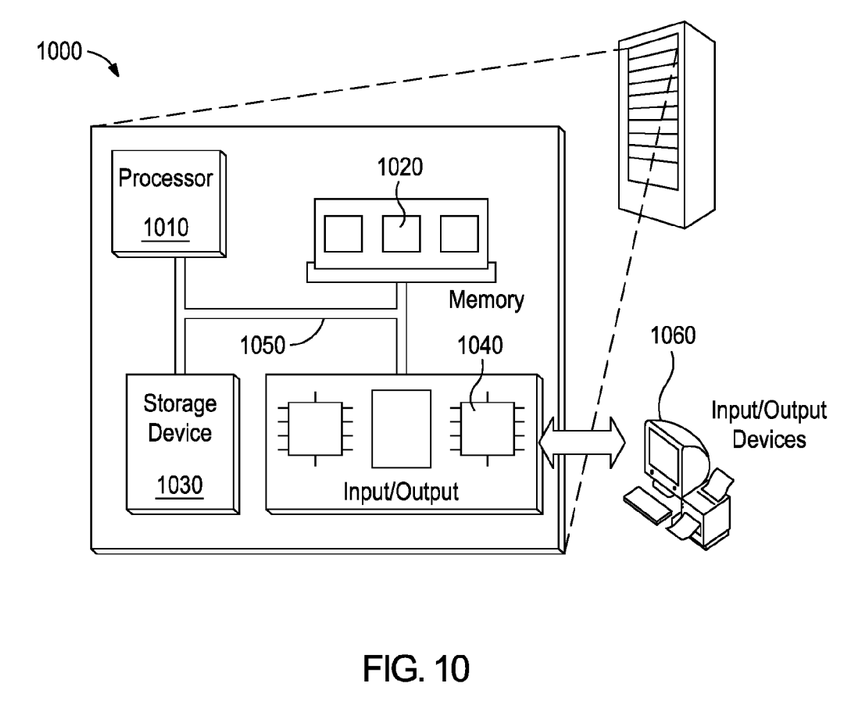
FIG. 10 illustrates an exemplary processing system for configuring and/or controlling a CT scanner and/or performing other tasks.

FIG. 10 shows an illustrative processing system 1000 for configuring and/or controlling a CT scanner that may obtain the CT images of the calibration disks 502a,b and/or the pellet 602, for analyzing the obtained CT images or performing other tasks as described herein. These analyses may determine whether the shaped charges may be used for hydraulic fracturing, the pellet design and manufacturing should be modified, or the samples should be rejected. Additionally, the analyses may permit maintaining a record of the pellet production and observe the production trends over time.

The system 1000 may include a processor 1010, a memory 1020, a storage device 1030, and an input/output device 1040. Each of the components 1010, 1020, 1030, and 1040 may be interconnected, for example, using a system bus 1050. The processor 1010 may be processing instructions for execution within the system 1000. In some embodiments, the processor 1010 is a single-threaded processor, a multi-threaded processor, or another type of processor. The processor 1010 may be capable of processing instructions stored in the memory 1020 or on the storage device 1030. The memory 1020 and the storage device 1030 can store information within the computer system 1000.

The input/output device 1040 may provide input/output operations for the system 1000. In some embodiments, the input/output device 1040 can include one or more network interface devices, e.g., an Ethernet card; a serial communication device, e.g., an RS-232 port; and/or a wireless interface device, e.g., an 802.11 card, a 3G wireless modem, or a 4G wireless modem. In some embodiments, the input/output device can include driver devices configured to receive input data and send output data to other input/output devices, e.g., keyboard, printer and display devices 1060. In some embodiments, mobile computing devices, mobile communication devices, and other devices can be used.

In accordance with at least some embodiments, the disclosed methods and systems related to scanning and analyzing material may be implemented in digital electronic circuitry, or in computer software, firmware, or hardware, including the structures disclosed in this specification and their structural equivalents, or in combinations of one or more of them. Computer software may include, for example, one or more modules of instructions, encoded on computer-readable storage medium for execution by, or to control the operation of, a data processing apparatus. Examples of a computer-readable storage medium include non-transitory medium such as random access memory (RAM) devices, read only memory (ROM) devices, optical devices (e.g., CDs or DVDs), and disk drives.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing, and grid computing infrastructures.

A computer program (also known as a program, software, software application, script, or code) can be written in any form of programming language, including compiled or interpreted languages, declarative, or procedural languages. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be executed on one computer or on multiple computers that are located at one site or distributed across multiple sites and interconnected by a communication network.

Some of the processes and logic flows described in this specification may be performed by one or more programmable processors executing one or more computer programs to perform actions by operating on input data and generating output. The processes and logic flows may also be performed by, and apparatus may also be implemented as, special purpose logic circuitry, e.g., an FPGA (field programmable gate array) or an ASIC (application specific integrated circuit).

Processors suitable for the execution of a computer program include, by way of example, both general and special purpose microprocessors and processors of any kind of digital computer. Generally, a processor will receive instructions and data from a read-only memory or a random access memory or both. A computer includes a processor for performing actions in accordance with instructions and one or more memory devices for storing instructions and data. A computer may also include, or be operatively coupled to receive data from or transfer data to, or both, one or more mass storage devices for storing data, e.g., magnetic, magneto optical disks, or optical disks. However, a computer may not have such devices. Devices suitable for storing computer program instructions and data include all forms of non-volatile memory, media and memory devices, including by way of example semiconductor memory devices (e.g., EPROM, EEPROM, flash memory devices, and others), magnetic disks (e.g., internal hard disks, removable disks, and others), magneto optical disks, and CD-ROM and DVD-ROM disks. The processor and the memory can be supplemented by, or incorporated in, special purpose logic circuitry.

To provide for interaction with a user, operations may be implemented on a computer having a display device (e.g., a monitor, or another type of display device) for displaying information to the user and a keyboard and a pointing device (e.g., a mouse, a trackball, a tablet, a touch sensitive screen, or another type of pointing device) by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A computer system may include a single computing device, or multiple computers that operate in proximity or generally remote from each other and typically interact through a communication network. Examples of communication networks include a local area network ("LAN") and a wide area network ("WAN"), an inter-network (e.g., the Internet), a network comprising a satellite link, and peer-to-peer networks (e.g., ad hoc peer-to-peer networks). A relationship of client and server may arise by virtue of computer programs running on the respective computers and having a client-server relationship to each other.

Embodiments disclosed herein include:

A. A method that includes positioning at least one calibration disk in a computed tomography (CT) scanner, the at least one calibration disk being made of a powder and exhibiting a known density, positioning a pellet in the CT scanner, the pellet being made of the powder, scanning the at least one calibration disk and the pellet using the CT scanner to obtain one or more CT images of the pellet and the at least one calibration disk, and comparing a density of the pellet with the known density of the at least one calibration disk based on the one or more CT images.

B. A method of examining an examination object that includes positioning at least one reference object having a known physical property in a computed tomography (CT) scanner, positioning the examination object in the CT scanner, the at least one reference object and the examination object being made of a similar material, scanning the at least one reference object and the examination object with the CT scanner to obtain at least one CT image, and comparing a physical property of the examination object with the known physical property of the reference object based on the at least one CT image.

C. A computer program product including a non-transitory computer readable medium having computer readable computer program code stored thereon that, when executed by a computer, configures the computer to scan at least one calibration disk and a pellet using a CT scanner to obtain one or more CT images of the pellet and the at least one calibration disk, and compare a density of the pellet at one or more locations of the pellet with a known density of the at least one calibration disk based on the one or more CT images, whereby a density value at the one or more locations is calculated.

Each of embodiments A, B, and C may have one or more of the following additional elements in any combination: Element 1: further comprising comparing the density of the pellet at one or more locations on or within the pellet to obtain a density value at the one or more locations.

Element 2: wherein the powder is an explosive powder and positioning the pellet in the CT scanner is preceded by introducing an amount of the explosive powder into a molding device, molding the explosive powder to form the pellet, and removing the pellet from the molding device. Element 3: wherein the molding device defines a shape of a shaped charge, the method further comprising molding the explosive powder such that a shape of the pellet matches the shape of the shaped charge. Element 4: wherein the molding device is a split die that includes a two-piece structure and removing the pellet from the molding device comprises separating the two-piece structure to remove the pellet. Element 5: wherein the powder is an explosive powder and positioning the at least one calibration disk in the CT scanner is preceded by placing a known mass of the explosive powder into a calibration disk tooling, pressing the known mass of the explosive powder with the calibration disk tooling under pressure to a known volume and thereby forming the at least one calibration disk, and removing the at least one calibration disk from the calibration disk tooling. Element 6: wherein the at least one calibration disk and the pellet are held in a CT fixture that includes a first disk fixture, a second disk fixture, and a pellet fixture, the CT fixture being made of a material having a density lower than the densities of the pellet and the at least one calibration disk, and the method further comprising placing the at least one calibration disk into the second disk fixture, stacking the first disk fixture atop the second disk fixture and seating a bottom of the pellet into the first disk fixture, lowering the pellet fixture around the pellet, and positioning the CT fixture in the CT scanner. Element 7: wherein the one or more CT images include the CT fixture, and the method further comprises excluding the CT fixture from the one or more CT images when calculating the density of the at least one calibration disk. Element 8: wherein each of the at least one calibration disk, the pellet, the first disk fixture, the second disk fixture, and the pellet fixture have a first set of orientation marks placed on them, and each of the first disk fixture, the second disk fixture, and the pellet fixture have a second set of orientation marks placed on them, the method further comprising aligning the first set of orientation marks align with each other and the second set of orientation marks align with each other when assembling the CT fixture. Element 9: wherein the powder is an explosive powder and the at least one calibration disk includes a first calibration disk and a second calibration disk, each being made of the explosive powder and each exhibiting a known density, the method further comprising positioning the first and second calibration disks in the CT scanner, scanning the first and second calibration disks and the pellet using the CT scanner to obtain the one or more CT images of the pellet and the first and second calibration disks, and comparing the density of the pellet with the known densities of the first and second calibration disks based on the one or more CT images. Element 10: wherein the known density of each of the first and second calibration disks is different.

Element 11: wherein the physical properties of the examination object and the at least one reference object are respective densities of the examination object and the at least one reference object, and the method further comprises comparing the density of the examination object with the known density of the at least one reference object using the at least one CT image, and calculating the density of the examination object based on the comparison. Element 12: further comprising molding the examination object from a material to form a first desired shape, placing the molded examination object in a CT fixture, and positioning the CT fixture including the molded examination object in the CT scanner. Element 13: further comprising molding a known mass of a material comprising the at least one reference object into a second desired shape of a known volume and thereby forming the at least one reference object, wherein the at least one reference object exhibits the known density, and placing the at least one reference object as molded into the second desired shape in the CT fixture. Element 14: wherein the at least one CT image includes the CT fixture, and the method further comprises excluding the CT fixture from the at least one CT image when calculating the density of the examination object.

Element 15: wherein the at least one calibration disk has a uniform density throughout. Element 16: wherein the at least one calibration disk and the pellet are held in a CT fixture made of a material having a density lower than the densities of the pellet and the at least one calibration disk, the computer program product further configuring the computer to exclude the CT fixture from the one or more CT images when calculating the density value at the one or more locations. Element 17: wherein the computer is further configured to simultaneously scan at least two calibration disks and the pellet using the CT scanner to obtain one or more CT images of the pellet and the at least two calibration disks, and compare the density of the pellet at one or more locations with a known density of each of the at least two calibration disks using the one or more CT images, the comparison providing the density value at the one or more locations.

By way of non-limiting example, exemplary combinations applicable to A, B, and C include: Element 2 with Element 3; Element 2 with Element 4; Element 6 with Element 7; Element 6 with Element 8; Element 9 with Element 10; Element 11 with Element 12; Element 12 with Element 13; and Element 12 with Element 14.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A method, comprising:
    positioning a first calibration disk in a computed tomography (CT) scanner, the first calibration disk being made of a powder and exhibiting a known density;
    positioning a pellet in the CT scanner, the pellet being made of the powder, wherein
        the first calibration disk and the pellet are held in a CT fixture that includes a first disk fixture, a second disk fixture, and a pellet fixture, and the CT fixture is made of a material having a density lower than the densities of the pellet and the first calibration disk, and
        the first disk fixture includes the pellet, the second disk fixture includes the first calibration disk, and the pellet fixture is positioned around the pellet;
    scanning the first calibration disk and the pellet using the CT scanner to obtain one or more CT images of the pellet and the first calibration disk; and
    comparing a density of the pellet with the known density of the first calibration disk based on the one or more CT images.

2. The method of claim 1, further comprising:
    comparing the density of the pellet at one or more locations on or within the pellet to obtain a density value at the one or more locations.

3. The method of claim 1, wherein the powder is an explosive powder and positioning the pellet in the CT scanner is preceded by:
    introducing an amount of the explosive powder into a molding device;
    molding the explosive powder to form the pellet; and
    removing the pellet from the molding device.

4. The method of claim 3, wherein the molding device defines a shape of a shaped charge, the method further comprising molding the explosive powder such that a shape of the pellet matches the shape of the shaped charge.

5. The method of claim 1, further comprising:
    determining colors of the one or more CT images of the pellet and the first calibration disk using a color scale; and
    determining the density of the pellet based on color differences between the one or more CT images of the pellet and the one or more CT images of the first calibration disk.

6. The method of claim 1, wherein the powder is an explosive powder and positioning the first calibration disk in the CT scanner is preceded by:
    placing a known mass of the explosive powder into a calibration disk tooling;
    pressing the known mass of the explosive powder with the calibration disk tooling under pressure to a known volume and thereby forming the first calibration disk; and removing the first calibration disk from the calibration disk tooling.

7. The method of claim 1, further comprising:
stacking the first disk fixture atop the second disk fixture and seating a bottom of the pellet into the first disk fixture;
lowering the pellet fixture around the pellet; and
positioning the CT fixture in the CT scanner.

8. The method of claim 7, wherein the one or more CT images include the CT fixture, and the method further comprises excluding the CT fixture from the one or more CT images when calculating the density of the first calibration disk.

9. The method of claim 7, wherein each of the first calibration disk, the pellet, the first disk fixture, the second disk fixture, and the pellet fixture have a first set of orientation marks placed on them, and each of the first disk fixture, the second disk fixture, and the pellet fixture have a second set of orientation marks placed on them, the method further comprising:
aligning the first set of orientation marks align with each other and the second set of orientation marks align with each other when assembling the CT fixture.

10. The method of claim 1, wherein the powder is an explosive powder and the CT fixture includes a third disk fixture, the method further comprising:
placing a second calibration disk in the third disk fixture;
stacking the second disk fixture atop the third disk fixture;
scanning the first and second calibration disks and the pellet using the CT scanner to obtain the one or more CT images of the pellet and the first and second calibration disks; and
comparing the density of the pellet with the known densities of the first and second calibration disks based on the one or more CT images.

11. The method of claim 10, wherein the known density of each of the first and second calibration disks is different.

12. A method of examining an examination object, comprising:
positioning at least one reference object having a known physical property in a computed tomography (CT) scanner;
positioning the examination object in the CT scanner, the at least one reference object and the examination object being made of a similar material, wherein
the at least one reference object and the examination object are held in a CT fixture that includes a first disk fixture, a second disk fixture, and an examination object fixture, and the CT fixture is made of a material having a density lower than the densities of the examination object and the at least one reference object, and
the first disk fixture includes the examination object, the second disk fixture includes the at least one reference object, and the examination object fixture is positioned around the examination object;
scanning the at least one reference object and the examination object with the CT scanner to obtain at least one CT image; and
comparing a physical property of the examination object with the known physical property of the reference object based on the at least one CT image.

13. The method of claim 12, wherein the physical properties of the examination object and the at least one reference object are respective densities of the examination object and the at least one reference object, and the method further comprises:
comparing the density of the examination object with the known density of the at least one reference object using the at least one CT image; and
calculating the density of the examination object based on the comparison.

14. The method of claim 13, further comprising:
molding the examination object from a material to form a first desired shape;
placing the molded examination object in a CT fixture; and
positioning the CT fixture including the molded examination object in the CT scanner.

15. The method of claim 14, further comprising:
molding a known mass of a material comprising the at least one reference object into a second desired shape of a known volume and thereby forming the at least one reference object, wherein the at least one reference object exhibits the known density; and
placing the at least one reference object as molded into the second desired shape in the CT fixture.

16. The method of claim 12, wherein the physical properties of the examination object and the at least one reference object are respective densities of the examination object and the at least one reference object, and the method further comprises:
determining colors of the one or more CT images of the examination object and the at least one reference object using a color scale; and
determining the density of the examination object based on color differences between the one or more CT images of the examination object and the one or more CT images of the at least one reference object.

17. A computer program product comprising a non-transitory computer readable medium having computer readable computer program code stored thereon that, when executed by a computer, configures the computer to:
scan a first calibration disk and a pellet using a CT scanner to obtain one or more CT images of the pellet and the first calibration disk, wherein
the first calibration disk and the pellet are held in a CT fixture that includes a first disk fixture, a second disk fixture, and a pellet fixture, and the CT fixture is made of a material having a density lower than the densities of the pellet and the first calibration disk, and
the first disk fixture includes the pellet, the second disk fixture includes the first calibration disk, and the pellet fixture is positioned around the pellet; and
compare a density of the pellet at one or more locations of the pellet with a known density of the first calibration disk based on the one or more CT images, whereby a density value at the one or more locations is calculated.

18. The computer program product of claim 17, wherein the computer program product further configures the computer to:
determine colors of the one or more CT images of the pellet and the first calibration disk using a color scale; and
determine the density of the pellet based on color differences between the one or more CT images of the pellet and the one or more CT images of the first calibration disk.

19. The computer program product of claim 17, wherein the computer is further configured to:
exclude the CT fixture from the one or more CT images when calculating the density value at the one or more locations.

20. The computer program product of claim 17, wherein the computer is further configured to:
 simultaneously scan the first calibration disk, a second calibration disk, and the pellet using the CT scanner to obtain one or more CT images of the pellet and the first and second calibration disks; and
 compare the density of the pellet at one or more locations with a known density of each of the first and second calibration disks using the one or more CT images, the comparison providing the density value at the one or more locations.

* * * * *